(12) United States Patent
Hasyagar et al.

(10) Patent No.: US 11,084,769 B2
(45) Date of Patent: Aug. 10, 2021

(54) PROCESS FOR ALDEHYDE REMOVAL FROM ALCOHOLS BY TREATMENT WITH BISULPHITE

(71) Applicant: SABIC Global Technologies B.V., Bergen op Zoom (NL)

(72) Inventors: Umesh Krishna Hasyagar, Bangalore (IN); Ritesh Nandy, Bangalore (IN); Vinod S. Nair, Bangalore (IN); Somak Paul, Riyadh (SA); Ibrahim S. Marhoon-Al, Jubail (SA)

(73) Assignee: SABIC GLOBAL TECHNOLOGIES B.V., Bergen op Zoom (NL)

( * ) Notice: Subject to any disclaimer, the term of this patent is extended or adjusted under 35 U.S.C. 154(b) by 0 days.

(21) Appl. No.: 16/644,593

(22) PCT Filed: Sep. 12, 2018

(86) PCT No.: PCT/IB2018/056977
§ 371 (c)(1),
(2) Date: Mar. 5, 2020

(87) PCT Pub. No.: WO2019/064107
PCT Pub. Date: Apr. 4, 2019

(65) Prior Publication Data
US 2021/0061739 A1   Mar. 4, 2021

Related U.S. Application Data

(60) Provisional application No. 62/563,463, filed on Sep. 26, 2017.

(51) Int. Cl.
*C07C 29/88* (2006.01)
*C07C 29/76* (2006.01)

(52) U.S. Cl.
CPC .............. *C07C 29/88* (2013.01); *C07C 29/76* (2013.01)

(58) Field of Classification Search
CPC .......... C07C 29/76; C07C 29/94; C07C 29/88
See application file for complete search history.

(56) References Cited

U.S. PATENT DOCUMENTS 2,641,543 A * 6/1953 Unger .................. C12H 1/0432
426/271
2,696,463 A * 12/1954 Baevsky .................. B01D 3/00
203/33

(Continued)

FOREIGN PATENT DOCUMENTS

GB          335683 A * 10/1930 ............. C07C 29/74
WO   WO-2015164414 A1 * 10/2015 ............... A61K 8/34
WO     WO2015164414 A1   10/2015

OTHER PUBLICATIONS

*Purification of Laboratory Chemicals* (6th Edt; Elsevier, 2009), p. 65, 752 pages.

(Continued)

*Primary Examiner* — Yate' K Cutliff
(74) *Attorney, Agent, or Firm* — Norton Rose Fulbright US LLP

(57) ABSTRACT

A method of purifying alcohol produced in a process that includes the Oxo process is disclosed. Aldehyde from the Oxo process that remains with the alcohol is removed by a reaction with an alkali sulphite to produce an insoluble adduct and alcohol having a reduced amount of aldehyde mixed with it. The adduct is removed from the alcohol by filtration.

20 Claims, 4 Drawing Sheets

(56) References Cited

U.S. PATENT DOCUMENTS 3,232,848 A      2/1966   Johnson
7,326,349 B2 *   2/2008   Asakawa ............. C12H 1/0432
                                                      210/264

OTHER PUBLICATIONS

International Search Report and Written Opinion from PCT/IB2018/056977 dated Dec. 12, 2018, 10 pages.
Bahrmann et al. "2-Ethylhexanol." Section "3. Industrial Production." Ullmann's Encyclopedia of Industrial Chemistry, Wiley-VCH Verlag GmbH & Co. KGaA, Weinheim, XP055525856, ISBN: 978-3-527-30673-2, DOI: 10.1002/14356007.a10_137.pub3, Jan. 1, 2013, 6 pages.

* cited by examiner

PROCESS FOR ALDEHYDE REMOVAL FROM ALCOHOLS BY TREATMENT WITH BISULPHITE

CROSS REFERENCE TO RELATED APPLICATIONS

This application is a national phase application under 35 U.S.C. § 371 of International Application No. PCT/IB2018/056977 filed Sep. 12, 2018, which claims priority to U.S. Provisional Patent Application No. 62/563,463 filed Sep. 26, 2017. The entire contents of each of the above-referenced disclosures is specifically incorporated by reference herein without disclaimer.

FIELD OF INVENTION

The present invention generally relates to a process for purifying alcohols. More specifically, the present invention relates to purifying alcohols by treatment with bisulphite.

BACKGROUND OF THE INVENTION

Some alcohols are made by converting olefins to their corresponding alcohols. In a process known as the Oxo process, first, an olefin is reacted with synthesis gas (carbon monoxide and hydrogen) to form an aldehyde (a hydroformylation reaction). Second, the aldehyde is aldolized to form an aldol. Third, the aldol is hydrogenated to form the alcohol. For example, 2-ethylhexanol is produced by hydroformylating propylene to form n-butyraldehyde, aldolizing the n-butyraldehyde to form hydroxyaldehyde followed by aldolizing the hydroxyaldehyde to form ethyl propyl acrolein (EPA), and hydrogenating the EPA to form 2-ethylhexanal and then hydrogenating the 2-ethylhexanal to form the 2-ethylhexanol.

In the process of making the alcohols by the Oxo process, some amount of aldehyde formed remains as one of the impurities in the alcohol. For example, in the production of 2-ethylhexanol, 2-ethylhexanal remains in the 2-ethylhexanol as an impurity. With this known aldehyde impurity of alcohols produced by the Oxo process, it should be noted that the 2-ethylhexanol end user market is shifting in Europe and the United States from di-octyl phthalate (DOP) to non-DOP segment (e.g., DOTP, TOTM, acrylate, etc.). Because of this shift, customers are strictly enforcing 2-ethylhexanol specifications with respect to aldehyde and peroxide content. Typically, the acceptable amount of aldehydes in 2-ethylhexanol is less than 500 parts per million (ppm) or less (300 ppm). During storage, however, even if the amount of aldehyde in 2-ethylhexanol is below 500 ppm, the amount of aldehyde in the 2-ethylhexanol can increase with time (e.g., an increase to >500 parts per million (ppm)). Consequently, the value of 2-ethylhexanol can decrease by the passage of time, for example, by just being in storage or just being transported from the production plant to market. Therefore, it is desirable to produce alcohols with aldehyde content well below 500 ppm so that when they enter the market the aldehyde content is still acceptable.

BRIEF SUMMARY OF THE INVENTION

A method has been discovered for purifying alcohols by using bisulphite to remove aldehyde—one of the primary contaminants of alcohol produced by the Oxo process, which includes the hydroformylation of an olefin to form the aldehyde. The bisulphite, according to embodiments of the invention, is reacted with the aldehyde that is in solution with the alcohol to form an adduct that is insoluble in the alcohol. The adduct can be separated from the alcohol by filtration, resulting in highly purified alcohol that has a small amount of aldehyde.

Embodiments of the invention include a method of purifying a liquid that comprises (1) primarily alcohol and (2) aldehyde. The method may include adding an alkali bisulphite to the liquid to form (a) an adduct and (b) remaining fluid. The method may further include separating the adduct from the remaining fluid by filtration, wherein the remaining fluid comprises less than 100 ppm aldehyde.

Embodiments of the invention include a method of purifying an alcohol that comprises (1) primarily 2-ethylhexanol and (2) 200 ppm to 2000 ppm aldehyde. The method may include adding sodium bisulphite to the alcohol and mixing the alcohol with the sodium bisulphite. The adding and the mixing forms (a) an adduct and (b) remaining fluid. The method may further include separating the adduct from the remaining fluid by filtration, wherein the remaining fluid comprises less than 50 ppm aldehyde.

The following includes definitions of various terms and phrases used throughout this specification.

The terms "about" or "approximately" are defined as being close to as understood by one of ordinary skill in the art. In one non-limiting embodiment the terms are defined to be within 10%, preferably, within 5%, more preferably, within 1%, and most preferably, within 0.5%.

The terms "wt. %", "vol. %" or "mol. %" refers to a weight, volume, or molar percentage of a component, respectively, based on the total weight, the total volume, or the total moles of material that includes the component. In a non-limiting example, 10 moles of component in 100 moles of the material is 10 mol. % of component.

The term "substantially" and its variations are defined to include ranges within 10%, within 5%, within 1%, or within 0.5%.

The term "primarily" and its variations are defined to mean at least 50%, e.g., 50.01 to 100%, or 51 to 90%.

The terms "inhibiting" or "reducing" or "preventing" or "avoiding" or any variation of these terms, when used in the claims and/or the specification, includes any measurable decrease or complete inhibition to achieve a desired result.

The term "effective," as that term is used in the specification and/or claims, means adequate to accomplish a desired, expected, or intended result.

The use of the words "a" or "an" when used in conjunction with the term "comprising," "including," "containing," or "having" in the claims or the specification may mean "one," but it is also consistent with the meaning of "one or more," "at least one," and "one or more than one."

The words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The process of the present invention can "comprise," "consist essentially of," or "consist of" particular ingredients, components, compositions, etc., disclosed throughout the specification.

In the context of the present invention, at least eighteen embodiments are now described. Embodiment 1 is a method of purifying a liquid that contains (1) primarily alcohol and (2) aldehyde. The method includes the steps of adding an alkali bisulphite to the liquid to form (a) an adduct and (b)

remaining fluid; separating the adduct from the remaining fluid by filtration, wherein the remaining fluid contains less than 100 ppm aldehyde. Embodiment 2 is the method of embodiment 1 further including the step of mixing the alcohol with the alkali bisulphite to form the adduct and the remaining fluid. Embodiment 3 is the method of embodiment 2 wherein the mixing is carried out for at least 30 minutes. Embodiment 4 is the method of any of embodiments 2 and 3, wherein the mixing is carried out by equipment that includes a stirrer. Embodiment 5 is the method of any of embodiments 2 to 4, wherein the mixing is carried out by equipment that includes a circulation system. Embodiment 6 is the method of any of embodiments 2 to 5, wherein the mixing is carried out by equipment that includes a continuous stirred tank reactor. Embodiment 7 is the method of any of embodiments 1 to 6, wherein formation of the adduct occurs at a temperature of 20° C. to 60° C. Embodiment 8 is the method of any of embodiments 1 to 7, wherein the liquid contains primarily 2-ethylhexanol. Embodiment 9 is the method of any of embodiments 1 to 8, wherein the alkali bisulphite is sodium bisulphite. Embodiment 10 is the method of any of embodiments 1 to 9, wherein the liquid contains 200 ppm to 2000 ppm aldehyde prior to the adding of the alkali bisulphite. Embodiment 11 is the method of any of embodiments 1 to 10, wherein the remaining fluid contains less than 50 ppm aldehyde. Embodiment 12 is the method of any of embodiments 1 to 11, wherein 50 wt. % to 95 wt. % of the aldehyde is removed from the liquid to form the remaining fluid. Embodiment 13 is the method of any of embodiments 1 to 12, wherein at least 90 wt. % of the aldehyde is removed from the liquid to form the remaining fluid. Embodiment 14 is the method of any of embodiments 1 to 13, wherein the method further includes the steps of forming the liquid by hydroformylating an olefin to form an aldehyde, aldolization of the aldehyde to form an aldol; and hydrogenating the aldol to form the alcohol in the liquid. Embodiment 15 is the method of embodiment 14, wherein the olefin is propylene and the alcohol formed is 2-ethylhexanol. Embodiment 16 is the method of any of embodiments 1 to 15, wherein the adding and the separating is carried out in a selection from the list consisting of a mobile storage tank, a stationary storage tank, a rail car tank, a truck tank, and a ship cargo tank.

Embodiment 17 is a method of purifying an alcohol that contains (1) primarily 2-ethylhexanol and (2) 200 ppm to 2000 ppm aldehyde. The method includes the steps of adding sodium bisulphite to the alcohol; mixing the alcohol with the sodium bisulphite, wherein the adding and the mixing forms (a) an adduct and (b) remaining fluid; and separating the adduct from the remaining fluid by filtration, the remaining fluid comprises less than 50 ppm aldehyde. Embodiment 18 is the method of embodiment 17 further including the step of hydroformylating propylene to form n-butyraldehyde; aldolizing the n-butyraldehyde to form hydroxyaldehyde and then aldolizing the hydroxyaldehyde to form ethylpropyl acrolein (EPA); and hydrogenating the EPA to form 2-ethylhexanal and then hydrogenating the 2-ethylhexanal to form the alcohol that contains primarily 2-ethylhexanol and 200 ppm to 2000 ppm aldehyde.

Other objects, features and advantages of the present invention will become apparent from the following figures, detailed description, and examples. It should be understood, however, that the figures, detailed description, and examples, while indicating specific embodiments of the invention, are given by way of illustration only and are not meant to be limiting. Additionally, it is contemplated that changes and modifications within the spirit and scope of the invention will become apparent to those skilled in the art from this detailed description. In further embodiments, features from specific embodiments may be combined with features from other embodiments. For example, features from one embodiment may be combined with features from any of the other embodiments. In further embodiments, additional features may be added to the specific embodiments described herein.

BRIEF DESCRIPTION OF THE DRAWINGS

For a more complete understanding, reference is now made to the following descriptions taken in conjunction with the accompanying drawings, in which.

DETAILED DESCRIPTION OF THE INVENTION

A method has been discovered for purifying alcohols by using bisulphite to remove aldehyde from alcohol produced by a process that includes the hydroformylation of an olefin to form the aldehyde. In the purification process, the aldehyde reacts with bisulphite to form an adduct. Because the adduct that is formed is insoluble in the alcohol, it can be separated by filtration from the alcohol.

Figure 1:
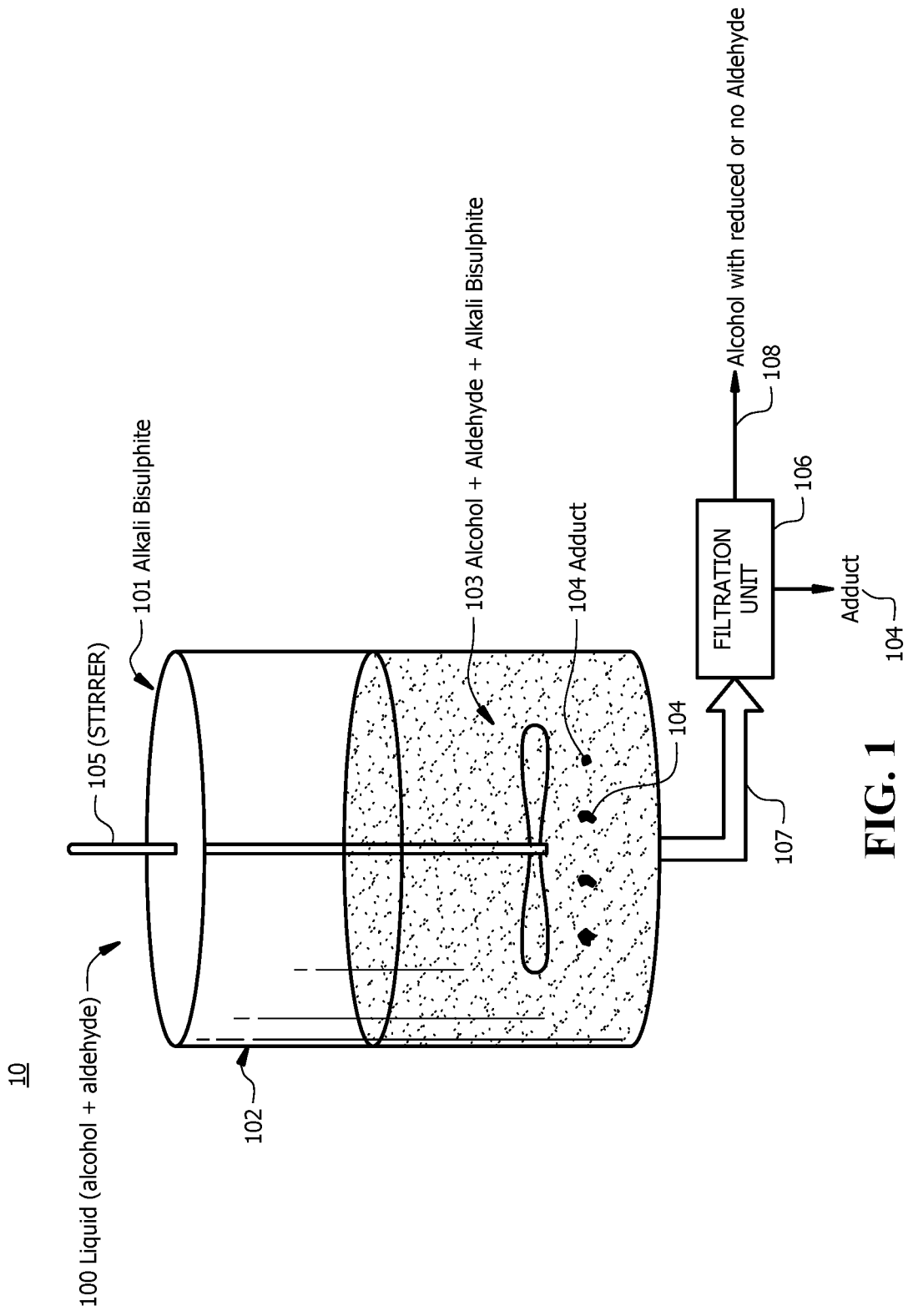
FIG. 1 shows a purification system for purifying a liquid comprising primarily alcohol, according to embodiments of the invention.
Figure 2:
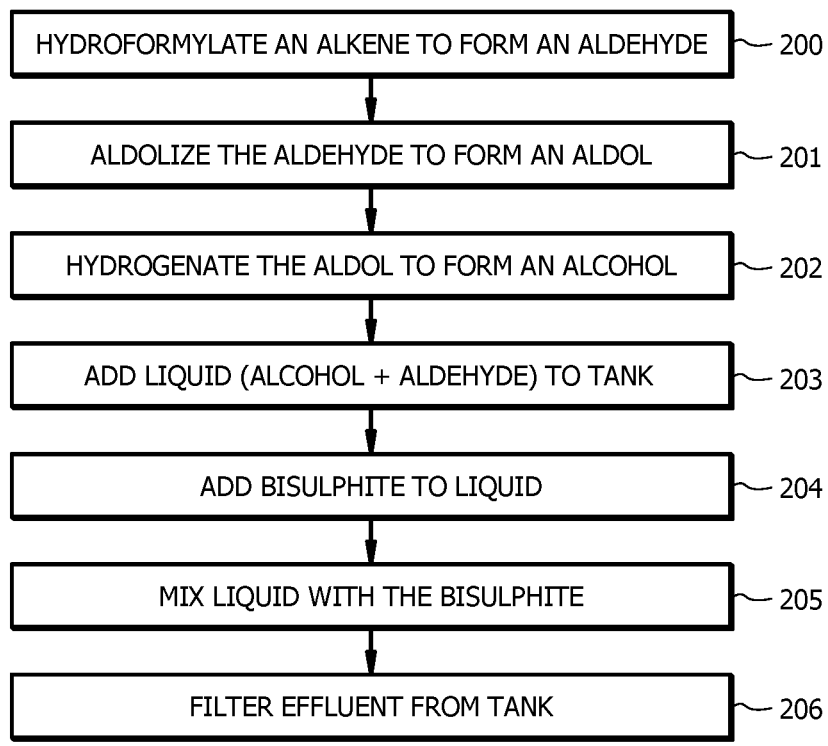
FIG. 2 shows a method for purifying a liquid comprising primarily alcohol, according to embodiments of the invention.

FIG. 1 shows purification system 10 for purifying a liquid comprising primarily alcohol, according to embodiments of the invention. FIG. 2 shows method 20 for purifying a liquid comprising primarily alcohol, according to embodiments of the invention. Method 20, or at least parts thereof, may be implemented by purification system 10.

As shown in FIG. 1, purification system 10 includes a tank 102, in which liquid 100 is introduced. According to embodiments of the invention, liquid 100 is produced by a process that includes the Oxo process. Thus, according to embodiments of the invention, method 20 may begin at block 200, which includes hydroformylation of an alkene to form an aldehyde. At block 201, the aldehyde is aldolized to form an aldol. The aldol may then be hydrogenated to form an alcohol, at block 202. The Oxo process produces primarily alcohol mixed with a relatively smaller amount of aldehyde as a product.

For example, in embodiments of the invention, the olefin that is hydroformylated at block 200 is propylene and the hydroformylation of the propylene forms n-butyraldehyde. The aldolization of the n-butyraldehyde, at block 201, forms hydroxyaldehyde followed by ethyl propyl acrolein (EPA). At block 202, EPA is hydrogenated to form 2-ethylhexanal and then to 2-ethylhexanol. But all the 2-ethylhexanal is typically not converted to 2-ethylhexanol. Rather, some of the 2-ethylhexanal remains mixed with the 2-ethylhexanol to form liquid 100. In embodiments of the invention, liquid 100 also includes one or more peroxides.

The amount of aldehyde in liquid 100, according to embodiments of the invention, may vary from 200 ppm to 2000 ppm aldehyde. Typically, liquid 100, which is produced by the Oxo process, which includes hydroformylation of an olefin, includes 99.5 to 99.85% alcohol, 20 to 500 ppm aldehyde, and 0.2 to 10 ppm peroxide. In embodiments of the invention, where propylene is the olefin that is hydroformylated, liquid 100 is a liquid that includes primarily 2-ethylhexanol and also includes a smaller amount of 2-ethylhexanal.

As shown in FIG. 2, method 20 may further include, at block 203, adding liquid 100 to tank 102. Tank 102 may be any type of storage tank that can contain liquid 100. At block 204, method 20 includes adding a bisulphite such as an alkali bisulphite to liquid 100. Embodiments of the invention may include the reverse, i.e., adding liquid 100 to the bisulphite in tank 102.

In embodiments of the invention, tank 102 may be equipped with stirrer 105, which may be used, at block 205, to mix liquid 100 (e.g., alcohol and aldehyde) with the alkali bisulphite to form mixture 103. In embodiments of the invention, liquid 100 may be mixed with the alkali bisulphite for a period of at least 30 minutes, preferably 1 to 2 hours. According to embodiments of the invention, as a result of contacting liquid 100 with alkali bisulphite and forming mixture 103, adduct 104 is formed by a reaction between the aldehyde in liquid 100 and the alkali bisulphite. In embodiments of the invention the mixing and the formation of adduct 104 occurs at a temperature of 20° C. to 60° C. In embodiments of the invention, liquid 100 includes primarily 2-ethylhexanol and 200 ppm to 2000 ppm aldehyde prior to the adding of the alkali bisulphite. The alkali bisulphite, in embodiments of the invention, is sodium bisulphite. When the alkali bisulphite is sodium bisulphite, the reaction with an aldehyde is represented as shown below:

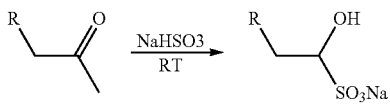

When adduct 104 is formed, remaining fluid 108 is also formed by the removal of material from liquid 100. Remaining fluid 108, according to embodiments of the invention, has less aldehyde than liquid 100. In embodiments of the invention, remaining fluid 108 comprises less than 100 ppm aldehyde, preferably less than 50 ppm aldehyde, and more preferably, less than 10 ppm aldehyde.

According to embodiments of the invention, adduct 104 is alpha-hydroxyalkyl sulphonic acid sodium salt and is not soluble in remaining fluid 108. Thus, remaining fluid 108, at block 206, may be separated from adduct 104 by feeding effluent from tank 102—effluent 107 (which includes adduct 104 and remaining fluid 108) to filtration unit 106, which carries out a filtration process. In embodiments of the invention, 80 wt. % to 95 wt. % of the aldehyde is removed from liquid 100 to form remaining fluid 108; more preferably, at least 90 wt. % of aldehyde is removed from liquid 100 to form remaining fluid 108. Remaining fluid 108, in embodiments of the invention, is either aldehyde free or has a reduced amount of aldehyde compared with liquid 100. The amount of aldehyde present in remaining fluid 108 may depend on the amount of time aldehyde (as a part of liquid 100) is mixed with the alkali bisulphite in tank 102 and/or the amount of alkali bisulphite added to tank 102. In embodiments of the invention, the ratio of alkali bisulphite added to aldehyde is in a range of 1.0 to 40 wt./wt.

Figure 3:
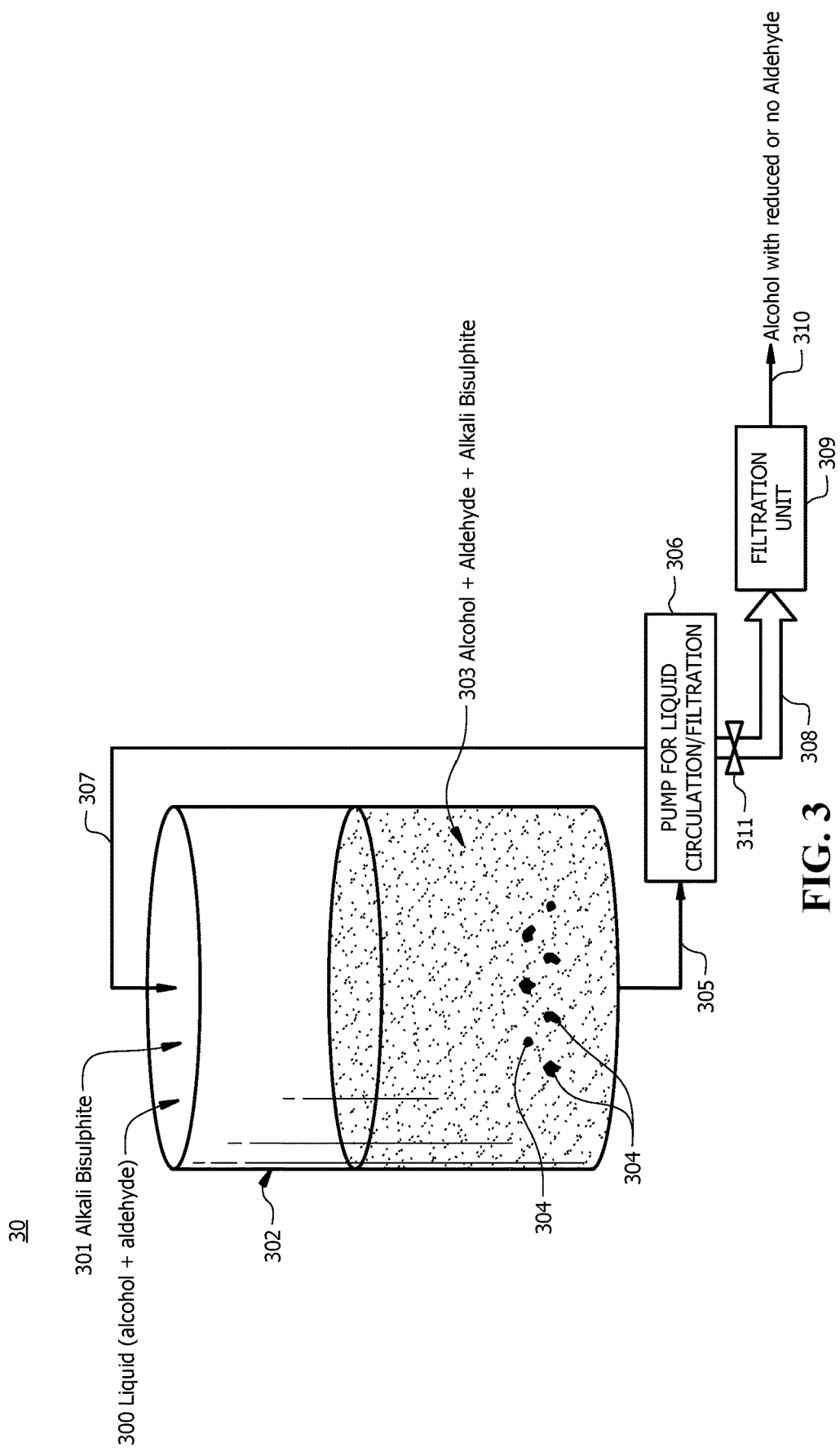
FIG. 3 shows a purification system for purifying a liquid comprising primarily alcohol, according to embodiments of the invention.
Figure 4:
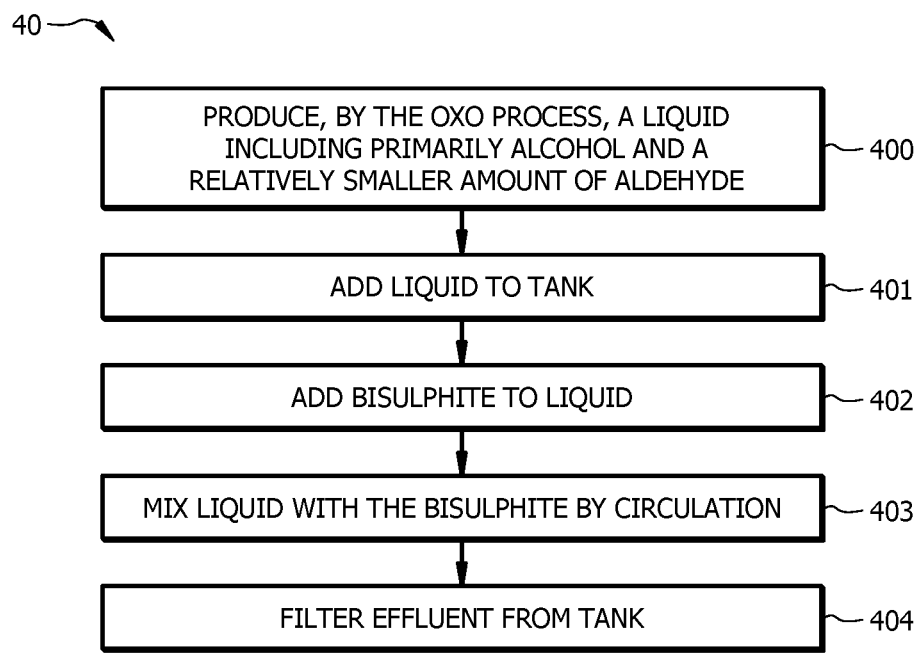
FIG. 4 shows a method for purifying a liquid comprising primarily alcohol, according to embodiments of the invention.

FIG. 3 shows purification system 30 for purifying a liquid comprising primarily alcohol, according to embodiments of the invention. FIG. 4 shows method 40 for purifying a liquid comprising primarily alcohol, according to embodiments of the invention. Method 40, or at least parts thereof, may be implemented by purification system 30. As shown in FIG. 3, purification system 30 includes tank 302, in which liquid 300 is introduced. According to embodiments of the invention, at block 400 of method 40, liquid 300 is produced by the Oxo process described above with respect to blocks 200 to 202 of method 20.

The amount of aldehyde in liquid 300, according to embodiments of the invention, may vary from 200 ppm to 2000 ppm aldehyde. Typically, liquid 300, which is produced by a process that includes hydroformylation of an olefin, includes 99.5 to 99.85% alcohol, 20 to 500 ppm aldehyde, and 0.2 to 10 ppm peroxide. In embodiments of the invention, where propylene is the olefin that is hydroformylated, liquid 100 is a liquid that comprises primarily 2-ethylhexanol and also includes a smaller amount of 2-ethylhexanal.

As shown in FIG. 4, method 40 may further include, at block 401, adding liquid 300 to tank 302. Tank 302 may be any type of storage tank that can contain liquid 300. At block 402, method 40 includes adding an alkali bisulphite to liquid 300. Embodiments of the invention may include the reverse, i.e., adding liquid 300 to alkali bisulphite in tank 302.

In embodiments of the invention, tank 302 may employ a circulation system, at block 403, to mix liquid 300 (e.g., alcohol and aldehyde) with an alkali bisulphite to form mixture 303. The circulation process may be implemented by pump 306, which is configured to pump effluent 305 from the bottom of tank 302 to the top of tank 302 via circulating line 307. While pump 306 is circulating effluent 305, valve 311 may be closed. In this way, mixture 308 (remaining fluid 310 and adduct 304) may be sent to filtration unit 309 only when sufficient amount of aldehyde has been removed from liquid 300 as a result of mixing it with bisulphite. When sufficient aldehyde has been removed from liquid 300, valve 311 is opened to allow mixture 308 to flow to filtration unit 309 to be filtered to produce aldehyde free/aldehyde reduced alcohol (remaining fluid 310). According to embodiments of the invention, valve 311 will be opened only when remaining fluid 310 meets a certain predetermined specification, i.e., a sufficiently low amount of aldehyde present.

In embodiments of the invention, liquid 300 may be mixed with the alkali bisulphite, by circulation for a period of at least 30 minutes, preferably 1 to 2 hours. According to embodiments of the invention, as a result of contacting liquid 300 with alkali bisulphite and forming mixture 303, adduct 304 is formed by a reaction between the aldehyde in liquid 300 and the alkali bisulphite. In embodiments of the invention the mixing and the formation of adduct 304 occurs at a temperature of 20° C. to 60° C. In embodiments of the invention, liquid 300 includes primarily 2-ethylhexanol and 200 ppm to 2000 ppm aldehyde prior to the adding of the alkali bisulphite. The alkali bisulphite, in embodiments of the invention, is sodium bisulphite. When the alkali bisulphite is sodium bisulphite, the reaction with an aldehyde is presented in the reaction shown by the chemical equation above.

When adduct 304 is formed, remaining fluid 310 is also formed by the removal of material from liquid 300. Remaining fluid 310, according to embodiments of the invention, has less aldehyde than liquid 300. In embodiments of the invention, remaining fluid 310 comprises less than 100 ppm aldehyde, preferably less than 50 ppm aldehyde, and more preferably, less than 10 ppm aldehyde.

According to embodiments of the invention, adduct 304 is alpha-hydroxyalkyl sulphonic acid sodium salt and is not soluble in remaining fluid 310. Thus, remaining fluid 310, at block 404, may be separated from adduct 304 by feeding effluent from pump 306—mixture 308 (which includes adduct 304 and remaining fluid 310) to filtration unit 309, which carries out a filtration process. In embodiments of the invention, 80 wt. % to 95 wt. % of the aldehyde is removed from liquid 300 to form remaining fluid 310; more preferably, at least 90 wt. % of aldehyde is removed from liquid 300 to form remaining fluid 310. In embodiments of the invention, the ratio of alkali bisulphite added to aldehyde is in a range of −1.0 to 40 wt./wt.

FIG. 3 shows that purification system 30 employs a circulation system for mixing while FIG. 1 shows that purification system 10 employs a stirrer. However, embodiments of the invention may employ both a stirrer and a circulation system. Further, embodiments of the invention may utilize a continuous stirred tank reactor as the mechanism for mixing the liquid to be purified with the bisulphite. Thus, the mixing of the liquid to be purified with the bisulphite according to embodiments of the invention may include different mixing systems that may include equipment selected from the list consisting of: a stirrer, a circulation system, a continuous stirred tank reactor, and combinations thereof.

In embodiments of the invention, the process of purifying as described in methods 20 and 40, including the adding and the separating, is carried out in a selection from the list consisting of: a mobile storage tank, a stationary storage tank, a rail car tank, a truck tank, and a ship cargo tank. In this way, the process according to embodiments of the invention, may be implemented at any point in the distribution chain, after production of the alcohol, so as to maintain the quality of the alcohol (i.e., establish a low level of aldehyde impurity) and achieve the maximum value for the alcohol product as possible when it is introduced in the market.

Although embodiments of the present invention have been described with reference to blocks of FIG. 2 and FIG. 4, it should be appreciated that operation of the present invention is not limited to the particular blocks and/or the particular order of the blocks illustrated in FIG. 2 and FIG. 4. Accordingly, embodiments of the invention may provide functionality as described herein using various blocks in a sequence different than that of FIG. 2 and FIG. 4.

EXAMPLE

As part of the disclosure of the present invention, a specific example is included below. The example is for illustrative purposes only and is not intended to limit the invention. Those of ordinary skill in the art will readily recognize parameters that can be changed or modified to yield essentially the same results.

Example

Purification of 2-ethylhexanol

A solution of 37 ml of 2 ethylhexanol having 361.27 ppm of aldehyde was stirred with 0.5 g of sodium sulphite for 1 hour at room temperature (25° C.). The mixture was filtered and analysed for aldehyde using gas chromatography (GC). The sodium bisulphite treated sample had 35 ppm of aldehyde, which corresponds to greater than 90% reduction of aldehyde (see Table 1).

TABLE 1

| Sample name | Avg Conc of aldehyde (ppm) |
| --- | --- |
| Feed | 361.27 |
| Treated sample | 35.68 |

The results of this example demonstrate that the concept of using sodium bisulphite in a treatment method to remove aldehyde from alcohols is effective.

Although embodiments of the present application and their advantages have been described in detail, it should be understood that various changes, substitutions and alterations can be made herein without departing from the spirit and scope of the embodiments as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the above disclosure, processes, machines, manufacture, compositions of matter, means, methods, or steps, presently existing or later to be developed that perform substantially the same function or achieve substantially the same result as the corresponding embodiments described herein may be utilized. Accordingly, the appended claims are intended to include within their scope such processes, machines, manufacture, compositions of matter, means, methods, or steps.

The invention claimed is:

1. A method of purifying a liquid, the method comprising:
adding an alkali bisulphite to the liquid, wherein the liquid comprises (1) at least 50% alcohol and (2) aldehyde and mixing the alcohol with the alkali bisulphite to form (a) an adduct and (b) remaining fluid; and
separating the adduct from the remaining fluid by filtration, wherein the remaining fluid comprises less than 100 ppm aldehyde, wherein formation of the adduct occurs at a temperature of 20° C. to 60° C.

2. The method of claim 1, wherein the mixing is carried out for at least 30 minutes.

3. The method of claim 1, wherein the mixing is carried out by equipment that includes a stirrer.

4. The method of claim 1, wherein the mixing is carried out by equipment that includes a circulation system.

5. The method of claim 1, wherein the mixing is carried out by equipment that includes a continuous stirred tank reactor.

6. The method of claim 1, wherein the liquid comprises primarily 2-ethylhexanol.

7. The method of claim 1, wherein the alkali bisulphite is sodium bisulphite.

8. The method of claim 1, wherein the liquid comprises 200 ppm to 2000 ppm aldehyde prior to the adding of the alkali bisulphite.

9. The method of claim 1, wherein the remaining fluid comprises less than 50 ppm aldehyde.

10. The method of claim 1, wherein 50 wt. % to 95 wt. % of the aldehyde is removed from the liquid to form the remaining fluid.

11. The method of claim 1, wherein at least 90 wt. % of the aldehyde is removed from the liquid to form the remaining fluid.

12. The method of claim 1, wherein the adding and the separating is carried out in a selection from the list consisting of: a mobile storage tank, a stationary storage tank, a rail car tank, a truck tank, and a ship cargo tank.

13. A method of purifying an alcohol that comprises (1) at least 50% 2-ethylhexanol and (2) 200 ppm to 2000 ppm aldehyde, the method comprising:

adding sodium bisulphite to the alcohol;

mixing the alcohol with the sodium bisulphite, wherein the adding and the mixing forms (a) an adduct and (b) remaining fluid; and separating the adduct from the remaining fluid by filtration, the remaining fluid comprises less than 50 ppm aldehyde.

14. The method of claim 13, wherein the alcohol comprises 200 ppm aldehyde.

15. The method of claim 1, wherein alcohol comprises (1) 2-ethylhexanol and (2) the aldehyde content of the liquid is 200 ppm to 2000 ppm, and wherein the remaining fluid comprises less than 50 ppm aldehyde.

16. A method of purifying a liquid, the method comprising:

adding an alkali bisulphite to the liquid, wherein the liquid comprises (1) at least 50% alcohol and (2) aldehyde, and mixing the alcohol with the alkali bisulphite to form (a) an adduct and (b) remaining fluid; and separating the adduct from the remaining fluid by filtration, wherein the remaining fluid comprises less than 100 ppm aldehyde, wherein formation of the adduct occurs at a temperature of 20° C. to 60° C.;

wherein the mixing is carried out for at least 30 minutes by equipment that includes a circulation system.

17. The method of claim 13, wherein the mixing is carried out for at least 30 minutes.

18. The method of claim 13, wherein the mixing is carried out by equipment that includes a circulation system.

19. The method of claim 13, wherein the mixing is carried out by equipment that includes a continuous stirred tank reactor.

20. The method of claim 17, wherein the mixing is carried out by equipment that includes a continuous stirred tank reactor.

* * * * *